United States Patent [19]  
Schmitz et al.

[11] 4,413,991  
[45] Nov. 8, 1983

[54] DUAL DOSE AMPULE

[76] Inventors: John B. Schmitz, 800 Fairview Ave., Arcadia, Calif. 91006; William L. Schmitz, 43901 Citrus View Dr., Hemet, Calif. 92343

[21] Appl. No.: 359,222

[22] Filed: Mar. 18, 1982

[51] Int. Cl.³ .............................................. A61M 5/00
[52] U.S. Cl. .................................................... 604/191
[58] Field of Search .......... 128/218 M, 218 F, 218 R, 128/218 N, 218 D, 218 DA, 215, 272.1, 272.3, 220, 221, 234

[56] References Cited  
U.S. PATENT DOCUMENTS

| 2,193,322 | 3/1940 | Lozier et al. | 128/218 M |
| 2,653,607 | 9/1953 | Deans | 128/218 M |
| 3,636,950 | 1/1972 | Gomez et al. | 128/218 M |
| 3,911,916 | 10/1975 | Stevens | 128/218 R |
| 4,031,892 | 6/1977 | Hurschman | 128/218 M |
| 4,040,420 | 8/1977 | Speer | 128/218 M |
| 4,171,698 | 10/1979 | Genese | 128/218 M |

Primary Examiner—John D. Yasko  
Attorney, Agent, or Firm—Allan D. Mockabee

[57] ABSTRACT

A method of an apparatus for hypodermically injecting at least two liquid medicaments which are kept separate from each other until use, and then causing them to be merged into a single pressurized flow stream in the lumen of a single hypodermic needle. Also, a liquid medicament ampule for plural medicaments, and a hypodermic needle carried in the ampule and isolated from the medicament compartments until use, to prevent possible corrosion of the needle by either or both of the medicaments.

6 Claims, 7 Drawing Figures

DUAL DOSE AMPULE

FIELD OF INVENTION

The invention lies in the field of hypodermic injection of plural medicaments, wherein the liquid medicaments are kept separate from each other until the actual time of injection.

PRIOR ART

While there are numerous devices for administering liquid medicaments hypodermically, the closest known to us are U.S. Pat. Nos. 3,136,313 Enstrom June 9, 1964; 4,194,505 Schmitz Mar. 23, 1980.

There is also an application for patent by William L. Schmitz and John B. Schmitz, Ser. No. 228,628 entitled Corrosive Protected Hypodermic Module in which the balance of issue fee was mailed to the Commmissioner of Patents and Trademarks Nov. 17, 1981.

The above patents show ampules for liquid medicaments which also have a hypodermic needle incorporated therewith, the ampules being adapted to be inserted in injector devices having spring powered mechanism for projecting the needle partially from the ampules and exerting pressure on the liquid medicaments to force them through the lumens of the needles. The above prior art devices, as well as any other less pertinent devices, all relate to the injection of a single liquid medicament. There are none known to us which are capable of injecting plural medicaments which are kept separate from each other until the time of actual injection.

Schmitz U.S. Pat. No. 4,194,505 discloses an ampule wherein the hypodermic needle is immersed in the medicament of the ampule until ready for use. This provides a compact ampule arrangement and maintains the needle in a sterile condition, but the arrangement disclosed in that patent cannot be used in conjunction with a liquid which has any tendency to contaminate the liquid and to corrode the metal of the needle, particularly the sharp point thereof. Furthermore, while our above identified allowed application for patent is directed to a device wherein the needle is isolated from the medicament until use, there is no concept of the use of two separated medicaments in a single ampule, accompanied by a single needle through which the plural liquids are injected.

DISCLOSURE

Toxic gases for use in warfare have been known for many years, and at times, have actually been used. In most instances these gases were toxic primarily if they were inhaled, although some of them are capable of creating skin irritation.

A more recent development in chemical warfare is what is commonly known as nerve gas, which is capable of acting upon the nervous system and causing death, even though only a relatively small surface area of the skin is exposed to the gas. Therefore the presently known and used gas mask is no defense to nerve gas attacks.

Nerve gas antidotes can be injected with hypodermic needles, preferably to save time and to keep from exposing the skin at the point of injection by causing the needle to penetrate the clothing and enter the tissue of the person affected or about to be affected by the gas. However, the antidotes comprised liquids, two or more in number, the liquids being kept separate from each other until the time of injection. Consequently, to equip a person with the antidote and means for administering it, would require a separate hypodermic needle for each of the liquid antidote substances. In the case of military personnel, where a needle injector device is carried on the person loaded with an ampule of antidote medicament, it would require a separate injector, ampule, and needle for each of the liquid constituents of the antidote. Not only would this hamper the movement of military personnel already loaded with various types of equipment, but would result in the expenditure of large sums of money for the duplicated injection devices which would have to be carried.

The present invention has as its general object to provide an ampule which can contain separate and unmixed substances comprising the antidote, with the needle associated therewith in such a manner that when the injector projects the needle forwardly, the plural liquid medicaments will be released from their separate compartments and injected through the lumen of a single hypodermic needle. The above and other objects of the invention will more fully appear from the following description in connection with the accompanying drawings.

Figure 1:
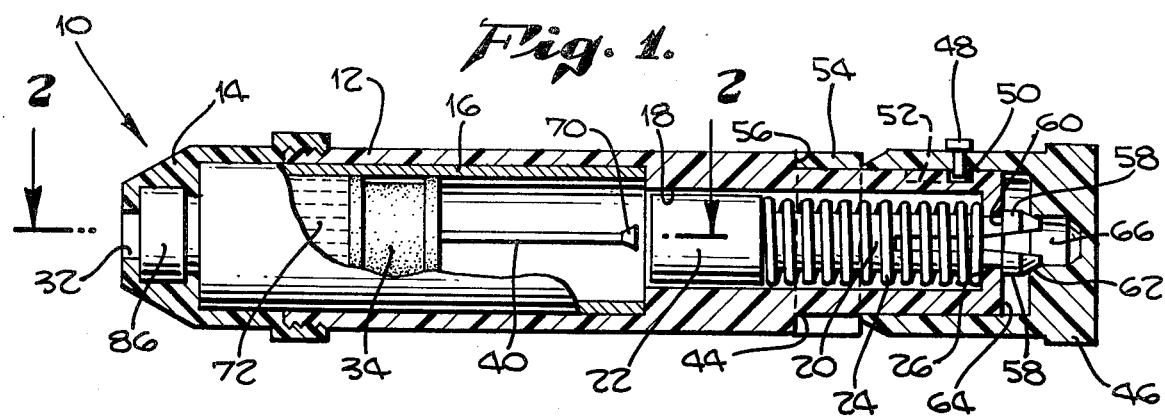
FIG. 1 is a longitudinal sectional view through an injector mechanism with an ampule in place therein.

An injector 10 shown in the above identified pending application, has a cylindrical casing 12 with a threadedly detachable end cap 14. The cylindrical chamber 12 is adapted to removably receive a cylindrical medicament ampule 16. Rearwardly of the ampule chamber 12 is a bore 18 to receive a shank 20 of a plunger 22. An expansion coil spring 24 is interposed between the rear side of the plunger 22 and the rear end wall 26 of the injector 10.

The cylindrical ampule 16 preferably has a reduced forward end 28 which has an open front end closed by a pierceable seal 30. In front of the seal 30 the end cap 14 is provided with an opening 32.

Within the cylindrical ampule 16 is a piston 34 of an elastomeric material provided with a bore 36 in which is slidably received a tubular needle guide 38 within which a needle 40 is slidable carried. Needle 70 is crimped at 40A to close the rear of the bore 36. The bore 36 terminates short of the front face of the piston 34 to provide a pierceable seal portion 42.

The injector 10 at its rearward portion is reduced as at 44 and upon this reduced portion is a cap 46 which is rotatable and longitudinally slidable upon the reduced portion 44. Rotational movement of the cap 46 is limited by a pin 48 in an arcuate slot 40 which lies partially about the circumference of said reduced portion. The slot 50, at one end thereof, connects with a short longitudinal slot 52. Also, just forward of the cap 46 is a split ring 54 which lies about the reduced portion 44 and between a shoulder 56 and the front end of cap 46. The split ring 54, which is removable, and the pin 48 provide double locking means to prevent accidental movement of the cap 46 for a reason to be explained below.

The rearwardly extending plunger shank 20 is split to provide catch knobs 58 having forwardly facing shoulder surfaces 60 and rearwardly disposed cam surfaces 62. The knobs 58 are biased away from each other.

The end closure 26 for the injector casing has an abutment surface 64 which faces rearwardly and engages the forwardly facing abutment surfaces 60 of the knobs 58 to hold the plunger shank 20 and the plunger in the position shown in FIG. 1 against the expansive action of the spring 24. The inside of cap 46 is provided with a recess 66 whose front edge cams against cam surfaces 62 to force the two knobs 58 toward each other and out of engagement with the abutment surface 64 on the rearend portion 26 of the injector casing. However, this can be done only after the split ring 56 has been removed.

Figure 5:
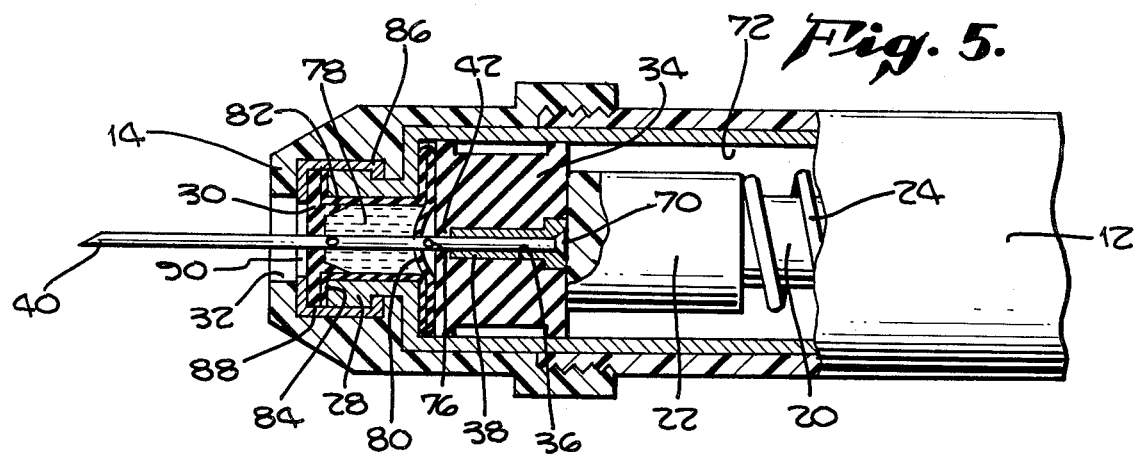
FIG. 5 is a view similar to FIG. 4 but with the needle in its final forwardly extended position.
Figure 6:
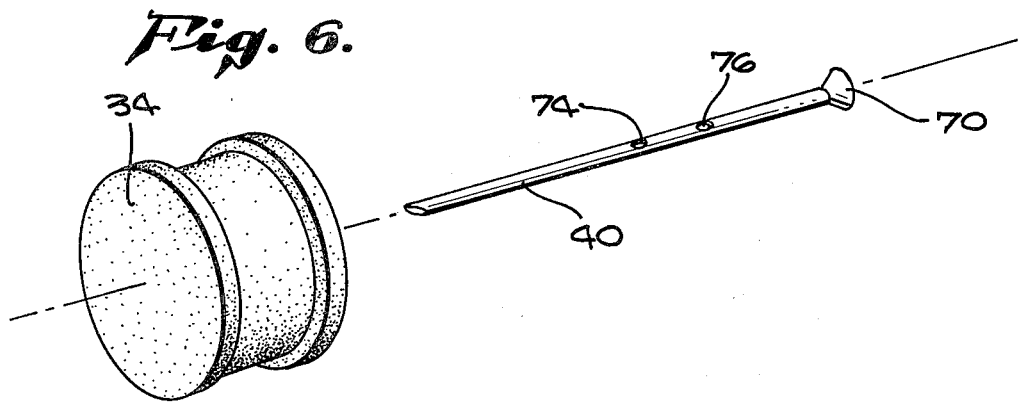
FIG. 6 is an exploded view of the piston and the hypodermic needle per se.

When the plunger 22 is thus released and projected forwardly as viewed in FIG. 5, the plunger will engage the enlarged end 70 of the hypodermic needle 40, causing it to move from the position of FIG. 1 ultimately to the position of FIG. 5. However, as soon as the plunger 22 hits the rear end of the needle 40, the forward end of the needle will be caused to pierce the sealing portion 42 of the piston 34 and enter a liquid medicament compartment 72.

Figure 3:
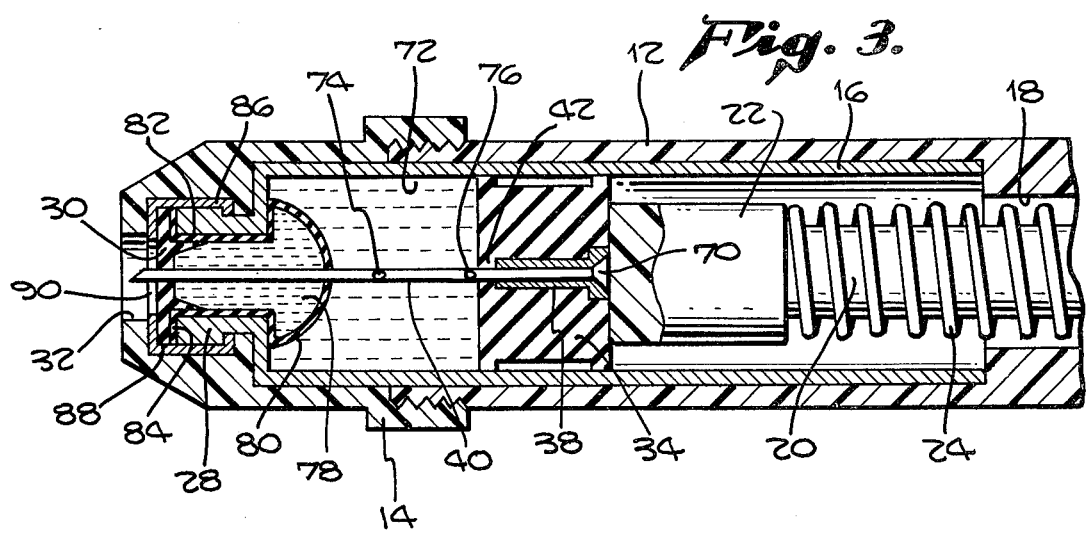
FIG. 3 is a view similar to FIG. 2 with the hypodermic needle in an intermediate position.

As the plunger 22 and needle 40 continue to move to the left, the right end of said needle will seat in the end of the guide 38 as illustrated in FIG. 3. In this position, it will be seen that the needle 40 has two inlet ports 74 and 76 which are located in the rearward medicament chamber 72 to admit medicament to the lumen or channel which extends through the front end of the needle 40 in the manner of the lumen of a conventional hypodermic needle. However, the lumen is closed at its rear end by crimping the rear end of the needle as at 40A.

Figure 4:
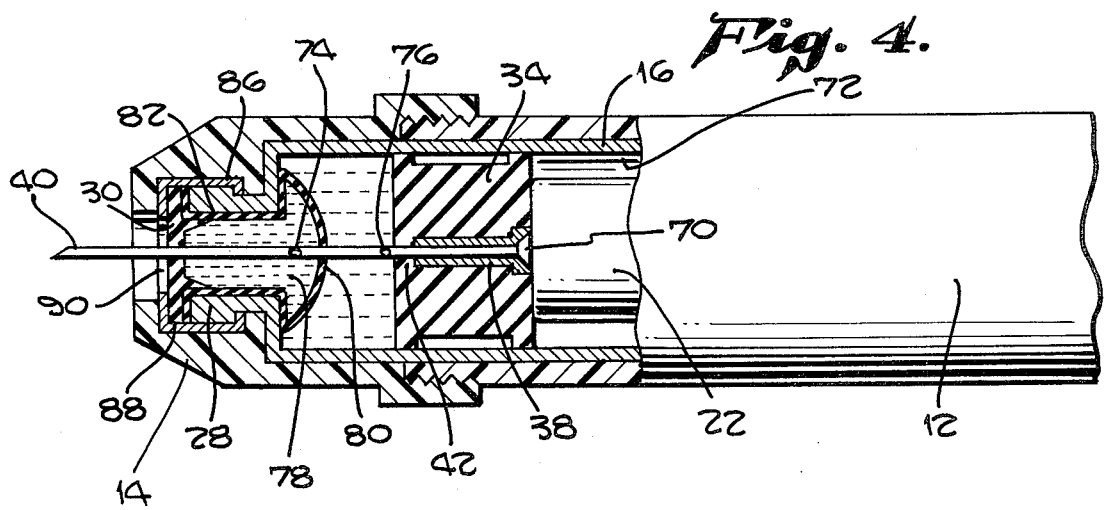
FIG. 4 is a view similar to FIGS. 2 and 3 with the inlet of the hypodermic needle in inlet flow with both medicament compartments.

The plunger 22 will move further forwardly under the influence of spring 24. When it reaches a position of FIG. 4, the lumen inlet port 76 is still located in the medicament compartment 72, while the inlet port 74 lies in a second medicament compartment 78, the needle 40 having pierced the pierceable rear wall or partition 80 which separates the medicament compartments 72 and 78. It will also be noted in FIGS. 3 and 4 that the forward end of the needle 40 will have pierced the end cap seal 30.

From the position of the plunger 22 and piston 34 in FIG. 3 to that of FIG. 5, the piston 34 will move forwardly, initially placing liquid medicament in the compartment 72 under pressure, and then as the needle inlet port 74 enters the forward medicament compartment 78, the liquid therein, being also under pressure, will cause the liquid medicament to flow from compartment 78 to the needle. Thus, while the two liquid medicament compartments are separate and sealed from each other until the time of use, said two liquids will form a single stream in the needle 40 and be injected together.

The reason for separating the two medicaments until the actual time of injection is not known to us. There may be some deleterious reaction between the two medicaments if they are maintained in mixed condition for any length of time, or it may be merely that the shelf life of the two when separated is greater than when they are mixed. Insofar as is known to us, it is not the practice to mix the two principal ingredients of nerve gas antidotes. An example of such an antidote is a combination of atropine and pralidoxime, generally in the chloride form. One ratio of the two medicaments is 0.7 ml. of atropine and 3.1 ml. of pralidoxime. It has been determined that atropine has a shelf life of approximately five years whereas that of pralidoxime chloride is approximately two years. We have been unable to determine whether the shelf life of the two in mixture would be less than two years or if some other problem would result. However, the fact remains that the two are not premixed and are brought together only at the time of injection.

The two chemicals can be injected separately but this would require an ampule of each chemical, with the need to reload the injector with a second ampule and perform two injection operations.

Another considerable advantage if injecting the two medicaments in one operation is that the needle insertion and injection is made through the clothing because it not only takes time to remove clothing to bare the skin for the injection, but it would result in the exposure of more skin to the effects of the gas during an attack.

The provision of the two liquid medicament compartments 72 and 78 is accomplished by the pierceable wall or partition 80 which forms part of a flexible sac-like element 82 which extends forwardly through the reduced forward end 28 of the cylindrical ampule 16. The forward edge portion 84 of the member 82 is held between the forward end of the ampule and the ampule seal 30. This assembly is held together by a metal band 86 which lies in the end cap 14 and is crimped about the reduced lower end of the ampule. In order to make a more complete seal, the seal 30 may have a circular flange 88 which extends into the mouth of the ampule and lies against an inner wall portion of the sac-like member 82. Thus when pressure is applied to the medicament in the compartment 78, the flange 88 will be pressed against the inner wall of said member 82. The crimped cap 86 has a central opening 90, providing ample room for the forward movement of the needle 40 after it pierces the seal 30.

Figure 7:
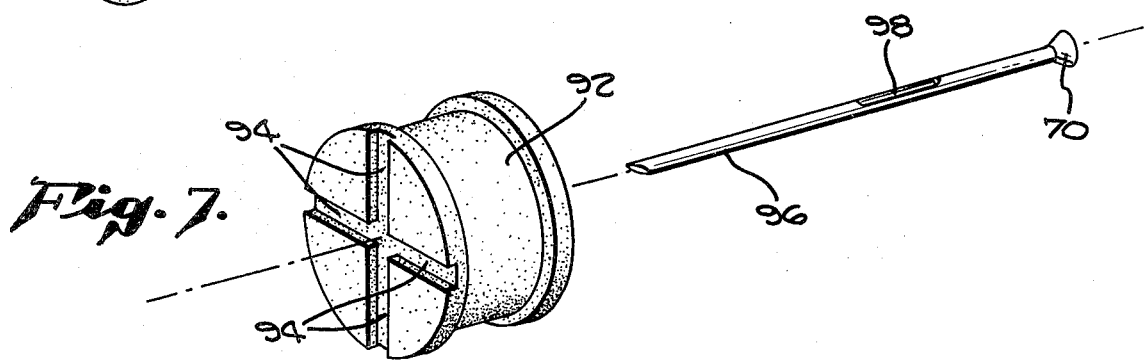
FIG. 7 is a view similar to FIG. 6 but with a modified form of the piston and needle.
Figure 2:
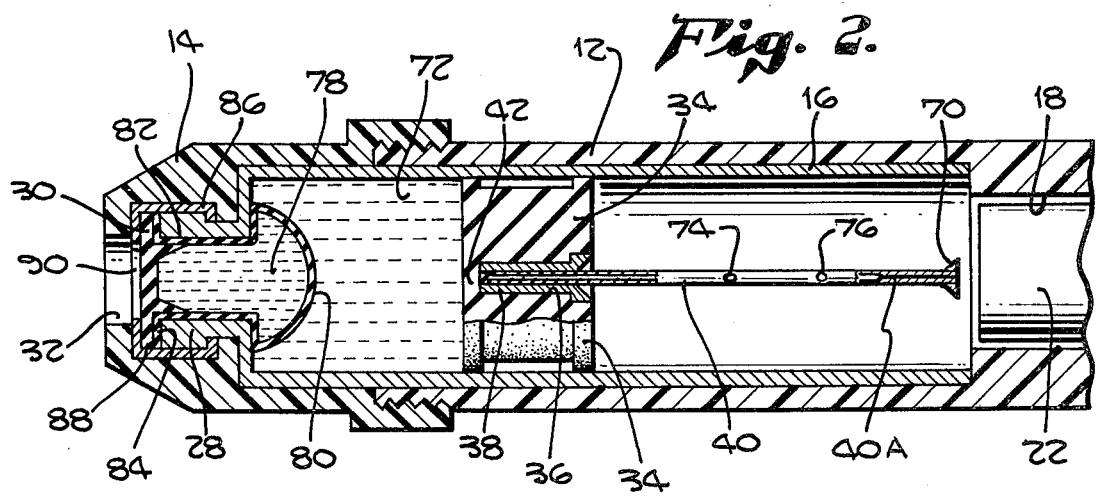
FIG. 2 is an enlarged section taken approximately on Line 22 of FIG. 1 showing the ampule and needle before actuation of the injector.

In FIG. 7 there is shown a modified form of piston 92 which is provided with grooves 94 in its front face to facilitate the flow of as much liquid as possible from the rearward medicament chamber 72, in which case the rearward inlet port 76 for the needle 40 would be positioned sufficiently rearward so that it would lie behind the pierceable wall or partition 80 when the plunger 92 is in the position of FIG. 5.

Also in FIG. 7 is a modified needle 96 which has a inlet port for the lumen of the needle in the form of an elongated slot 98. This would enlarge the inlet port means and permit more rapid liquid flow into it through most of the stroke of the piston 34 or piston 92.

From the needle position of FIG. 1 until the needle 40 has moved forwardly to a position where it is about to pierce the end cap seal 30, the needle is not filled with liquid because there is equal pressure at the tip of the needle and at the inlet port 74 or 76. However, when the needle tip pierces the seal 30 and penetrates the clothing and skin of the subject, the liquid pressure balance in the needle is broken and liquid will be forced through inlet ports 74 and 76, then through the needle and out of its end during the movement of the needle into the tissue of the patient. Because liquid is being forced through the needle during its movement into the tissue, a considerable percentage of the liquid medicament is distributed in the tissue throughout the path or movement of the needle so that there is no large concentration of liquid pressure and disruption of tissue at the point of deepest penetration of the needle. This manner of injection liquid medicaments is known as track injection, and while it is shown in my prior patent and application, it is a highly desirable type of injection.

While the invention is shown and described as having two compartments for liquid medicament, it should be understood that it is within the concept of this invention to provide additional medicament compartments with extra needle inlet ports such as ports 74 and 76, or a needle such as needle 96 in FIG. 7, which could be provided wih a single inlet port 98 of greater elongation.

While the structure shown in the drawings provides tandem medicament compartments in front of the needle in its ready position, it is to be understood that the positional arrangement of the medicament compartments can be varied, the only requirement being that actuation of the device produce pressurized flow of the plural medicaments into a common stream in the hypodermic needle for injection. Also, other changes may be made in the form details arrangement and proportions of the structure without departing from the spirit of the invention.

What is claimed is:

1. A dual dose liquid medicament device comprising:
a tubular chamber having rearward and forward ends,
a hypodermic needle supported in said chamber for forward movement therein between a rearward limit and a forward limit with the forward end of the needle extending from said chamber,
said hypodermic needle having a lumen with a forward outlet and with rearward inlet means,
a pair of separate liquid medicament compartments in said chamber,
means for flowing liquid medicaments from both compartments to said lumen inlet means,
a wall in said chamber pierceable by the hypodermic needle and dividing a portion of said chamber into said separate liquid medicament compartments,
said compartments being in tandem axially of said chamber,
and both compartments having pierceable walls other than said wall dividing a portion of said chamber in the said separate liquid medicament compartments,
and said hypodermic needle in its rearward limit of movement, having its forward end located rearwardly of both said compartments.

2. The structure in claim 1, and means associated with said chamber for moving the forward end of said hypodermic needle forwardly through said compartments and beyond the forward end of said chamber.

3. The structure in claim 1, and means for moving the forward end of said needle forwardly through said compartments and beyond the forward end of said chamber, and means for applying pressure to said liquid medicament compartments to cause liquid medicament to flow through said lumen inlet means when said needle is moved forwardly.

4. A corrosive portected dual dose hypodermic device comprising:
a cylindrical chamber open at its forward end,
a pierceable wall across said forward end of said chamber,
a piston in said chamber in slidable sealed relation to the interior wall of the chamber,
said chamber, between said pierceable seal and said piston having a pair of liquid medicaments compartments,
said piston having a longitudinal bore there through,
a pierceable diaphragm across the forward end of said bore, sealing the bore from said medicament compartments,
a tissue piercing hypodermic needle having a lumen with an open forward portion and rearward inlet means and supported in said bore behind the pierceable diaphragm and longitudinally slidable in said bore and through said compartments,
means for flowing liquid medicaments from both compartments to said lumen inlet means,
a needle guide slidably mounted in said bore,
said tissue piercing needle being slidably mounted in said guide and extending rearwardly therefrom,
and the rear end of said needle having a transverse dimension greater than the inner diameter of said needle guide.

5. The structure in claim 4, and said needle having a transverse dimension greater than the inner diameter of said needle guide.

6. The structure in claim 4, and said guide extending rearwardly from said bore and the rear of said piston, said needle having its forward end in the forward end of said guide adjacent the rear of said pierceable diaphragm,
said cylindrical barrel having an open rear end,
an injector comprising a housing receiving said cylindrical chamber and having an open forward end,
said injector having a spring loaded plunger therein movable from a position adjacent the rear end of said cylindrical chamber to a position forwardly in said chamber,
and a trigger device in operative association with said spring loaded plunger to release the plunger and permit it to be propelled forwardly in said cylindrical chamber.

* * * * *